(12) United States Patent
Ducke et al.

(10) Patent No.: US 9,867,729 B2
(45) Date of Patent: Jan. 16, 2018

(54) ENDOGRAFT INTRODUCER AND A CAPSULE ASSEMBLY FOR AN ENDOGRAFT INTRODUCER

(71) Applicant: Cook Medical Technologies LLC, Bloomington, IN (US)

(72) Inventors: Werner D. Ducke, Eight Mile Plains (AU); David Ernest Hartley, Wannanup (AU); David Sean O'Brien, Cullendore (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/612,682

(22) Filed: Feb. 3, 2015

(65) Prior Publication Data

US 2015/0216694 A1 Aug. 6, 2015

(30) Foreign Application Priority Data

Feb. 5, 2014 (AU) .................................. 2014200686

(51) Int. Cl.
*A61F 2/95* (2013.01)
*A61F 2/962* (2013.01)
*A61F 2/966* (2013.01)
*A61F 2/07* (2013.01)

(52) U.S. Cl.
CPC ................ *A61F 2/966* (2013.01); *A61F 2/95* (2013.01); *A61F 2/07* (2013.01); *A61F 2002/9665* (2013.01)

(58) Field of Classification Search
CPC .... A61F 2/966; A61F 2/07; A61F 2/95; A61F 2002/9665
See application file for complete search history.

(56) References Cited

U.S. PATENT DOCUMENTS

| 7,867,270 | B2 | 1/2011 | Hartley et al. | |
|---|---|---|---|---|
| 8,034,074 | B2 | 10/2011 | Garner et al. | |
| 2003/0233101 | A1* | 12/2003 | Lubock | A61M 37/0069 606/116 |
| 2007/0106324 | A1* | 5/2007 | Garner | A61F 2/013 606/200 |
| 2007/0265694 | A1 | 11/2007 | Sarac et al. | |

(Continued)

FOREIGN PATENT DOCUMENTS

WO 2009148602 A1 12/2009

*Primary Examiner* — Jing Ou
(74) *Attorney, Agent, or Firm* — Richard J. Godlewski

(57) ABSTRACT

A capsule assembly for an endograft introducer is disclosed. The assembly comprises: a capsule retriever having a plug portion and a tail portion, the plug portion having a lead-in surface, the tail portion having an elongate body extending proximally from the plug portion to an end stop feature receiver; a capsule tube having an end stop feature at a proximal end thereof and terminating in a distal end, the end stop feature and the end stop receiver arranged such that proximal movement of the capsule tube relative to the plug portion is limited; and a capsule cavity inside the capsule tube, a proximal end of a prosthesis being receivable in the cavity. The capsule tube is slidably movable with respect to the capsule retriever to a position in which the distal end of the capsule tube is adjacent to the lead-in surface of the plug portion.

22 Claims, 10 Drawing Sheets

(56) References Cited

U.S. PATENT DOCUMENTS

| | | | |
|---|---|---|---|
| 2008/0033354 A1* | 2/2008 | Hartley | A61F 2/95 604/103.05 |
| 2008/0065011 A1* | 3/2008 | Marchand | A61F 2/2433 604/103.02 |
| 2009/0099637 A1 | 4/2009 | Barthold et al. | |
| 2009/0192518 A1 | 7/2009 | Golden et al. | |
| 2010/0100167 A1* | 4/2010 | Bortlein | A61F 2/2436 623/1.11 |
| 2010/0198328 A1 | 8/2010 | Hartley et al. | |
| 2011/0144735 A1* | 6/2011 | Hartley | A61F 2/95 623/1.11 |
| 2011/0307048 A1* | 12/2011 | Ivancev | A61F 2/07 623/1.11 |
| 2012/0226341 A1 | 9/2012 | Schreck et al. | |

* cited by examiner

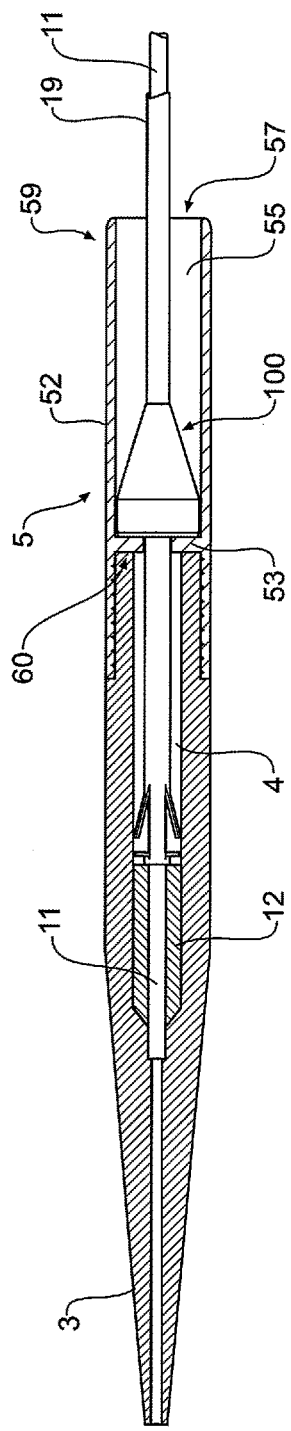
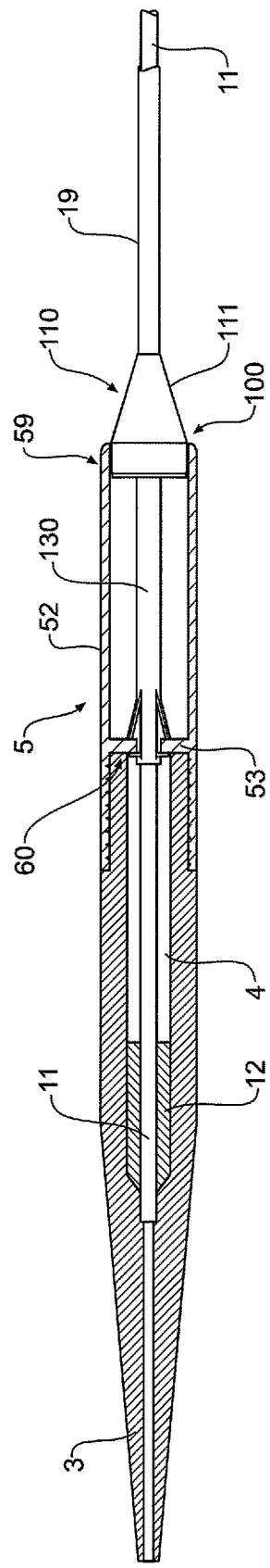
Figure 1A
Figure 1B

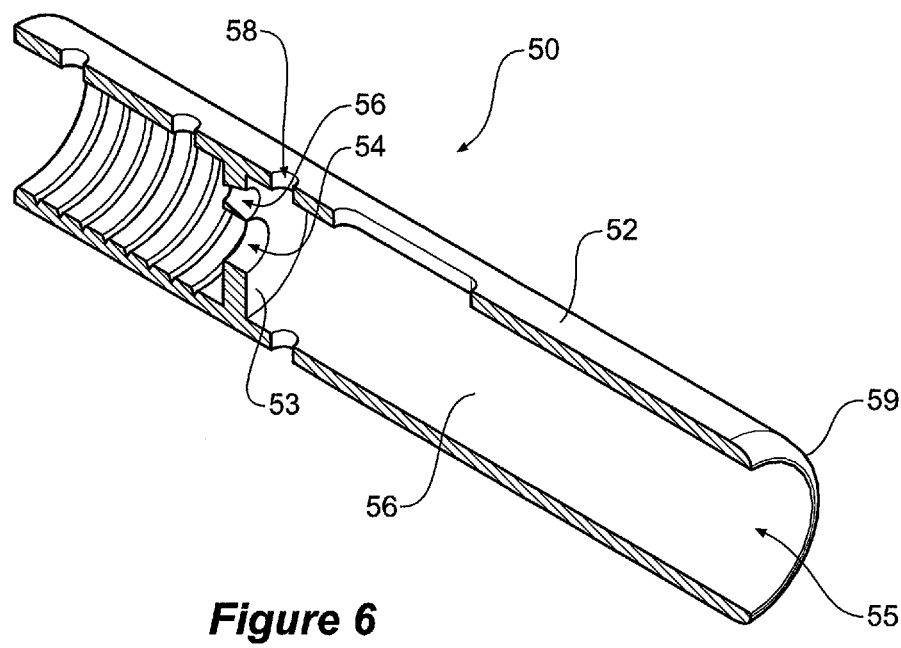
Figure 6
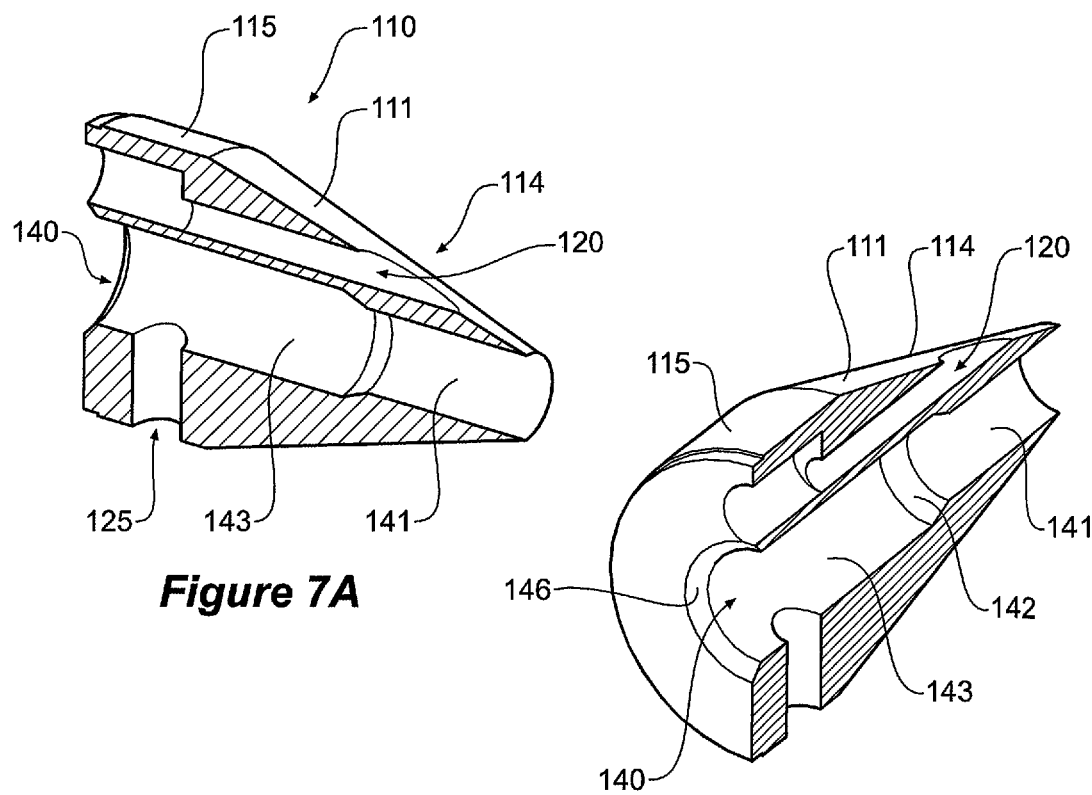
Figure 7A
Figure 7B

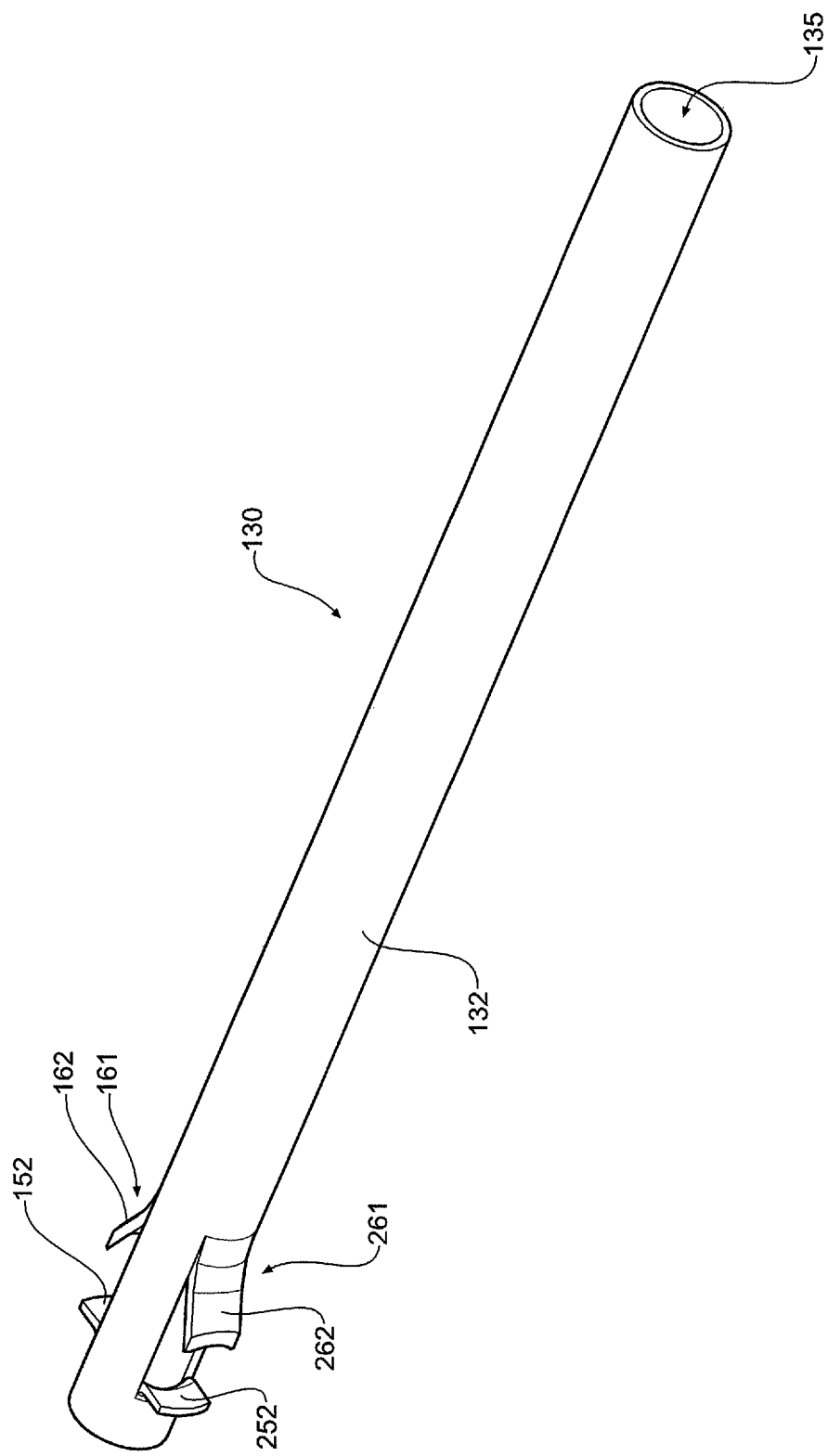

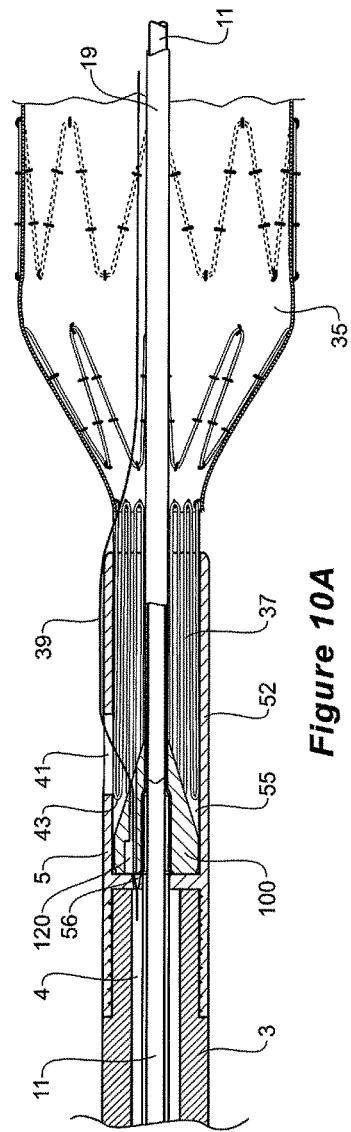
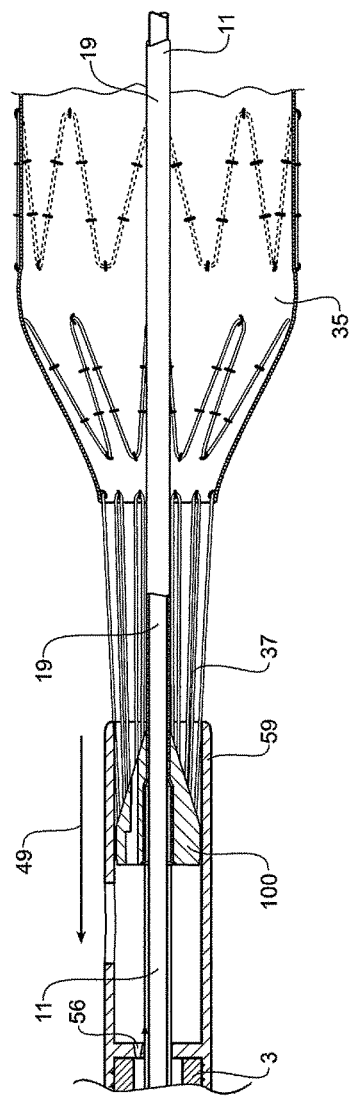
Figure 10A
Figure 10B

ENDOGRAFT INTRODUCER AND A CAPSULE ASSEMBLY FOR AN ENDOGRAFT INTRODUCER

TECHNICAL FIELD

The invention relates to medical devices and more particularly to a medical device used for deployment of an intraluminal graft or stent graft, otherwise referred to as an introducer or a stent graft introducer. In particular, this invention relates to a top cap retrieval arrangement.

BACKGROUND

In the deployment of a graft, or stent graft, into the human or animal body via intraluminal techniques, a deployment device is used to introduce the stent graft into a lumen of the body and, after the stent graft has been deployed and expanded within the lumen, the introducer needs to be retracted.

One form of introducer uses a proximal nose cone with a distally facing capsule to encompass an exposed stent and barbs extending from the exposed stent of a stent graft during introduction and, after the stent graft has been released and the capsule has been removed from the exposed stent, the capsule along with the introducer must be withdrawn. The capsule, however, typically has a distally facing opening with an edge surrounding it and this edge can engage with stents of the deployed stent graft and potentially cause problems by dislodging the stent graft from its position on the wall of the lumen.

It is known to provide moveable capsule plugs to facilitate retrieval of introducers. However, known capsule assemblies comprising capsules and capsule plugs, have various shortcomings.

Throughout this specification, the term distal with respect to a portion of the aorta, a deployment device or an endograft means the end of the aorta, deployment device or endograft further away in the direction of blood flow away from the heart and the term proximal means the portion of the aorta, deployment device or end of the endograft nearer to the heart. When applied to other vessels, similar terms such as caudal and cranial should be understood.

SUMMARY

According to a first aspect of the invention, there is provided a capsule assembly for an endograft introducer, the capsule assembly comprising:
  a capsule retriever having a plug portion and a tail portion, the plug portion having a lead-in surface, the tail portion having an elongate body extending proximally from the plug portion to an end stop feature receiver;
  a capsule tube having an end stop feature at a proximal end thereof and terminating in a distal end; and
  a capsule cavity inside the capsule tube, a proximal end of a prosthesis being receivable in the cavity,
  wherein the capsule tube is slidably movable with respect to the capsule retriever from a first position in which the distal end of the capsule tube surrounds an opening into the capsule cavity to a second position in which the distal end of the capsule tube is adjacent to the lead-in surface of the plug portion and the end stop feature and end stop feature receiver are engaged.

In one form, the end stop feature comprises a capsule wall, the capsule wall defining a wall aperture.

In one form, the lead-in surface includes a frusto-conical portion.

In one form, the plug portion comprises a landing surface proximally adjacent to the lead-in surface, the landing surface slidably engaging the capsule tube.

In one form, the tail portion comprises a tail lock, the tail lock arranged to prevent the lead-in surface of the capsule plug portion re-entering the capsule tube from the second position.

In one form, the tail lock comprises a barb, the barb extending proximally from the elongate body and terminating with a barb abutment surface, the barb abutment surface resiliently moveable from a relaxed position to a deflected position, the deflected position enabling the abutment surface to pass through the wall aperture.

In one form, when the capsule tube is in the second position, the abutment surface is prevented from re-entering the wall aperture by abutment of the abutment surface against the end wall.

In one form, the tail portion comprises a tail tube, the tail tube defining a tail lumen.

In one form, the tail tube comprises a pair of opposed resiliently flexible tabs, each tab forming a said barb.

In one form, the tail tube comprises a pair of opposed flanges, the flanges forming said end stop receiver.

In one form, the barbs and the flanges and the tube are a unitary assembly.

According to a second aspect of the invention, there is provided a system for delivering and deploying an expandable prosthesis, the system comprising:
  a sheath having a lumen;
  a delivery catheter including a longitudinally extending guide wire catheter, the delivery catheter slidably disposed within the lumen of the sheath;
  an expandable prosthesis disposed on a proximal portion of the delivery catheter;
  a haemostatic device sealingly engaging the delivery catheter; and
  a capsule assembly at the proximal portion of the delivery catheter, the capsule assembly comprising:
    a capsule retriever having a plug portion and a tail portion, the plug portion having a lead-in surface, the tail portion having an elongate body extending proximally from the plug portion to an end stop feature receiver;
    a capsule tube having an end stop feature at a proximal end thereof and terminating in a distal end; and
    a capsule cavity inside the capsule tube, a proximal end of a prosthesis being receivable in the cavity,
  wherein the capsule tube is slidably movable with respect to the capsule retriever from an first position in which the distal end of the capsule tube surrounds an opening into the capsule cavity to a second position in which the distal end of the capsule tube is adjacent to the lead-in surface of the plug portion and the end stop feature and end stop feature receiver are engaged.

In one form, the system further comprises a plug sleeve joined to the capsule plug portion and mounted coaxially around the guide wire catheter, the guide wire catheter slidably movable with respect to the plug sleeve and the capsule plug portion from the first position to the second position.

In one form, the end stop feature comprises a capsule wall, the capsule wall defining a wall aperture.

In one form, the tail portion comprises a tail lock, the tail lock arranged to prevent the lead-in surface of the capsule plug portion re-entering the capsule tube from the second position.

In one form, the tail lock comprises a barb, the barb extending proximally from the elongate body and terminating with a barb abutment surface, the barb abutment surface resiliently moveable from a relaxed position to a deflected position, the deflected position enabling the abutment surface to pass through the wall aperture.

In one form, when the capsule tube is in the second position, the abutment surface is prevented from re-entering the wall aperture by abutment of the abutment surface against the end wall.

In one form, the tail portion comprises a tail tube, the tail tube defining a tail lumen.

In one form, the tail tube comprises a pair of opposed resiliently flexible tabs, each tab forming a said barb.

In one form, the tail tube comprises a pair of opposed flanges, the flanges forming said end stop receiver.

According to a third aspect of the invention, there is provided a system for delivering and deploying an expandable prosthesis, the system comprising:
a sheath having a lumen;
a delivery catheter including a longitudinally extending guide wire catheter, the delivery catheter slidably disposed within the lumen of the sheath;
an expandable prosthesis disposed on a proximal portion of the delivery catheter;
a haemostatic device sealingly engaging the delivery catheter; and
a capsule assembly at the proximal portion of the delivery catheter, the capsule assembly comprising:
a capsule tube terminating in a distal end;
a proximal capsule end wall, the end wall defining a wall aperture and an end stop feature;
a capsule cavity generally bounded by the capsule tube and the proximal capsule end wall, a proximal end of a prosthesis being receivable in the cavity; and
a capsule retriever having a plug portion and a tail portion, the plug portion having a lead-in surface, the tail portion having an elongate body extending proximally from the plug portion through the wall aperture and having an end stop feature receiver, the end stop feature and end stop feature receiver mutually engagable.

According to a fourth aspect of the invention, there is provided an endograft introducer comprising a nose cone dilator and a capsule assembly at a proximal end, a guide wire catheter extending distally from the nose cone dilator though the capsule assembly, a sheath and a handle, to a distal end, the capsule assembly as defined by claim 1.

BRIEF DESCRIPTION OF DRAWINGS

Embodiments of the present invention will be discussed with reference to the accompanying drawings wherein:

FIGS. 1A and 1B are diagrammatic cross-sectional views showing a capsule assembly in a first position and in a second position respectively;

FIG. 6 is a cut-away isometric view of a capsule that forms part of the capsule assembly shown in FIG. 5;

FIGS. 7A and 7B show a plug portion of the capsule retriever shown in FIG. 4 in cut-away cross-sectional views;

FIGS. 8A and 8B are isometric views of a tail portion of the capsule retriever shown in FIG. 4;

FIGS. 10A, 10B and 10C show a proximal end of a stent graft retained, being released and released respectively from the capsule assembly of FIGS. 1A and 1B.

DESCRIPTION OF EMBODIMENTS

Figure 3:
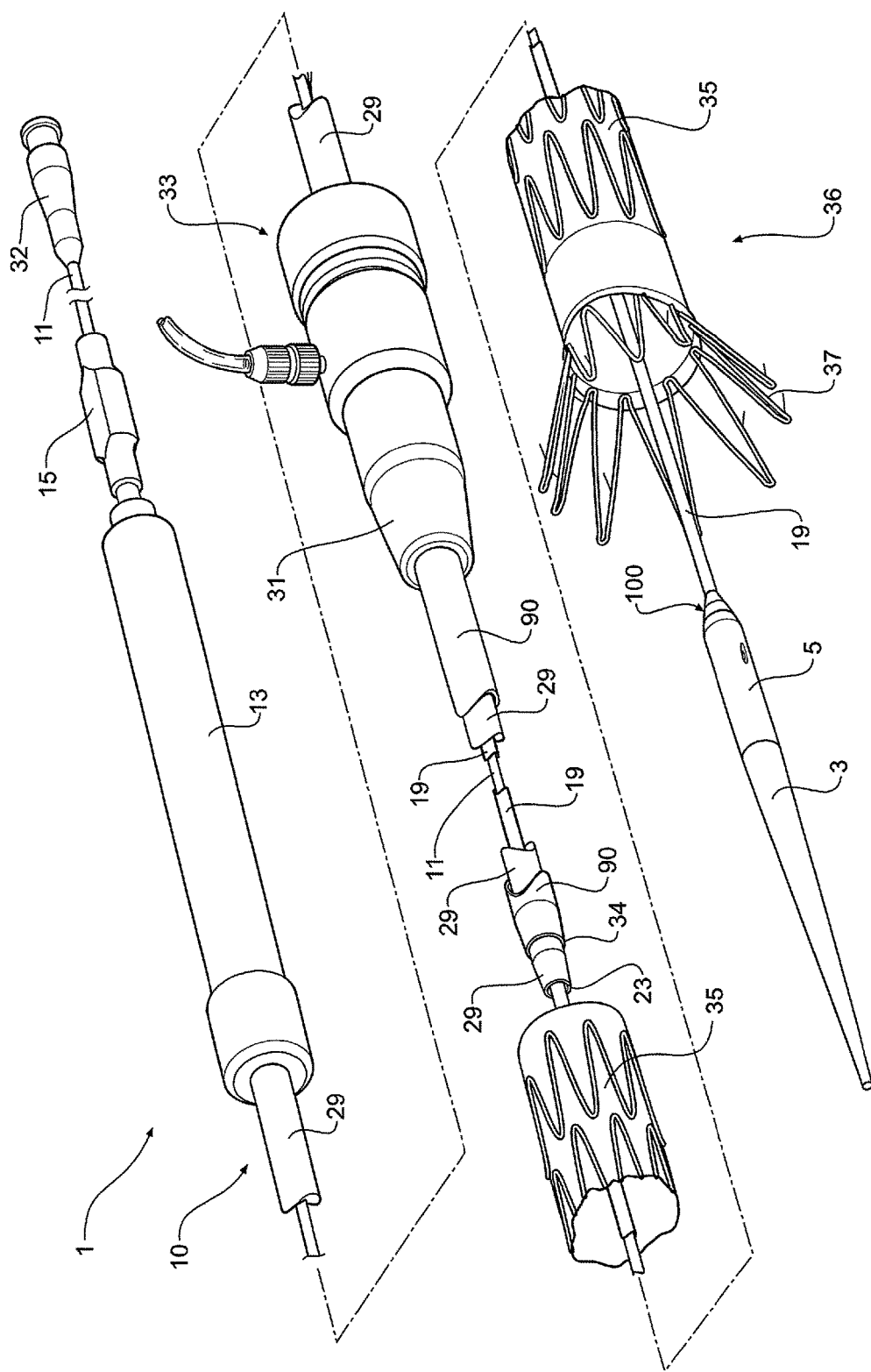
FIG. 3 is an isometric view of a stent graft on a delivery device upon which the capsule assembly of FIGS. 1A and 1B is mounted.
Figure 5:
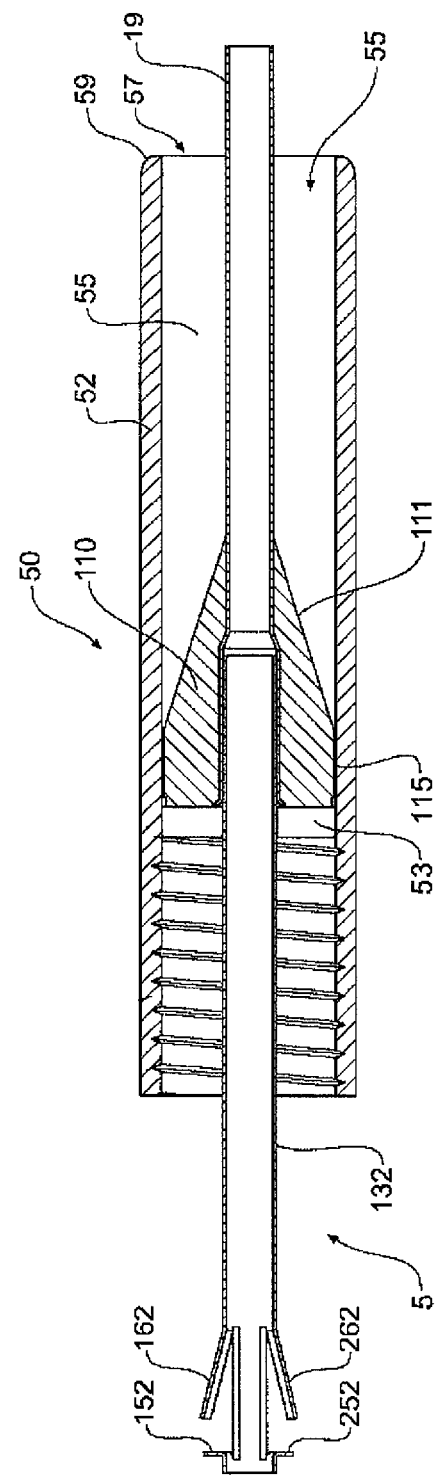
FIG. 5 is a similar view to that of FIG. 4 but shows additional components of the capsule assembly.

Referring to FIGS. 1A, 1B and FIG. 3, a capsule assembly 5 for an endograft introducer is shown. The introducer 1 is shown in FIG. 3 together with an endograft in the form of a stent graft 35. The capsule assembly 5 comprises a capsule tube 52 terminating in a distal end 59. The assembly further comprises an end stop feature 60 in the form of a proximal capsule end wall 53, the end wall defining a wall aperture 54 that is most clearly shown in FIG. 6. As can be seen in FIG. 5, a capsule cavity 55 is generally bounded by the capsule tube 52 and the proximal capsule end wall 53.

A proximal end 36 of a prosthesis 35 is shown in FIG. 3, the proximal end 36 being receivable in the cavity 55. More specifically, in the example shown in FIG. 3, exposed stents 37 at the proximal end of the stent graft 35 are received in the cavity 55 shown in FIGS. 5 and 10A.

Referring again to FIG. 4, a capsule retriever 100, having a plug portion 110 and tail portion 130, is shown. The plug portion 110 has a lead-in surface 111. This lead-in surface 111 provides a lead-in for the entire capsule assembly 5 and nose cone dilator 3 when in the position shown in FIGS. 1B and 10C.

The capsule retriever 100 also has a tail portion 130 having an elongate body in the form of a tail tube 132 extending proximally from the plug portion 110 through the wall aperture 54, shown most clearly in FIG. 6. The tail portion 130 also has an end stop feature receiver 150 most clearly shown in FIGS. 4 and 5. The wall aperture 54 and the end stop feature receiver 150 are arranged such that proximal movement of the capsule 50 and hence the capsule tube 52 relative to the plug portion 110 is limited. More specifically, proximal movement of the capsule 50 and hence the capsule tube 52 relative to the plug portion 110 is limited by the end stop feature 60 and end stop feature receiver 150 engaging each other.

Turning to FIGS. 7A and 7B, the plug portion 110 is shown in more detail. The plug portion 110 comprises a landing surface 115, which slidably engages the capsule tube 52, as is most clearly shown in FIG. 5. The capsule tube 52 is slidably movable with respect to the capsule retriever 100 from a first position, shown in FIG. 1A, in which the distal end 59 of the capsule tube 52 surrounds an opening 57 into the capsule cavity 55, to a second position, shown in FIG.

Figure 10C:
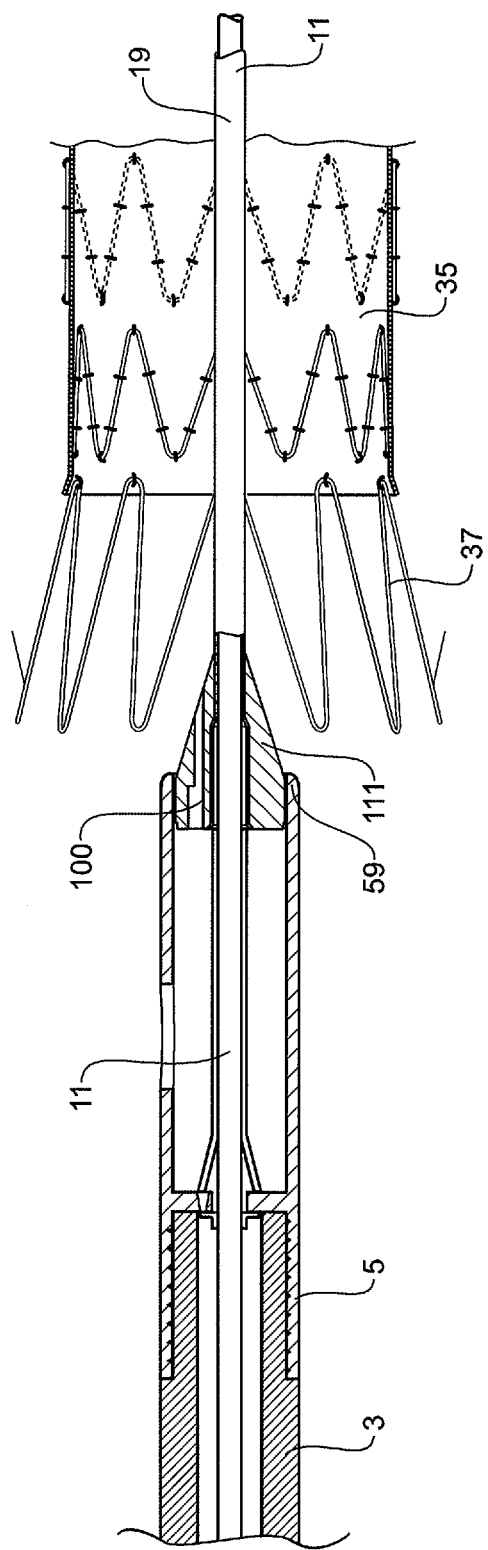

1B, in which the distal end 59 of the capsule tube 52 is adjacent to the plug portion 110. This arrangement provides a transition from the lead-in surface 111 of the plug portion 110 to the distal end 59 of the capsule tube 52, as is shown in FIGS. 1B and 10C. The capsule assembly 5 may be made from radiopaque nylon or any other suitable material.

Referring to FIGS. 5 and 6, it can be seen that the capsule tube 52 is a relatively simple component that is easy to manufacture. Compared to some prior art devices, tight tolerance are less important. Furthermore, there is no change in the internal diameter of the capsule cavity 55, where the proximal end 36 of the stent graft 35 is enclosed. This reduces the chance of catching. Finally, the capsule 50 design allows for the capsule tube 52 to have a thicker peripheral wall which, in turn, means that it is less likely to be distorted by tension in the trigger wire 39.

The plug portion 110 has a trigger wire lumen 120, most clearly shown in FIG. 7A, for a trigger wire 39, as is shown in FIG. 10A.

With the embodiments shown in the drawings, and in particular FIGS. 7A and 7B, the lead-in surface 111 of the plug portion 110 includes a frusto-conical portion 114. In other embodiments, not shown, the lead-in surface may be bullet-shaped or any suitable shape so as to provide a lead-in for the capsule assembly 5 as it is retracted distally away from the heart back towards the introduction site. The external surface of the plug portion 10 is relatively straight forward in its shape. There are no large steps in the diameter that could catch on features of the capsule tube 52 for instance. This provides advantages over prior art devices.

Figure 8B:
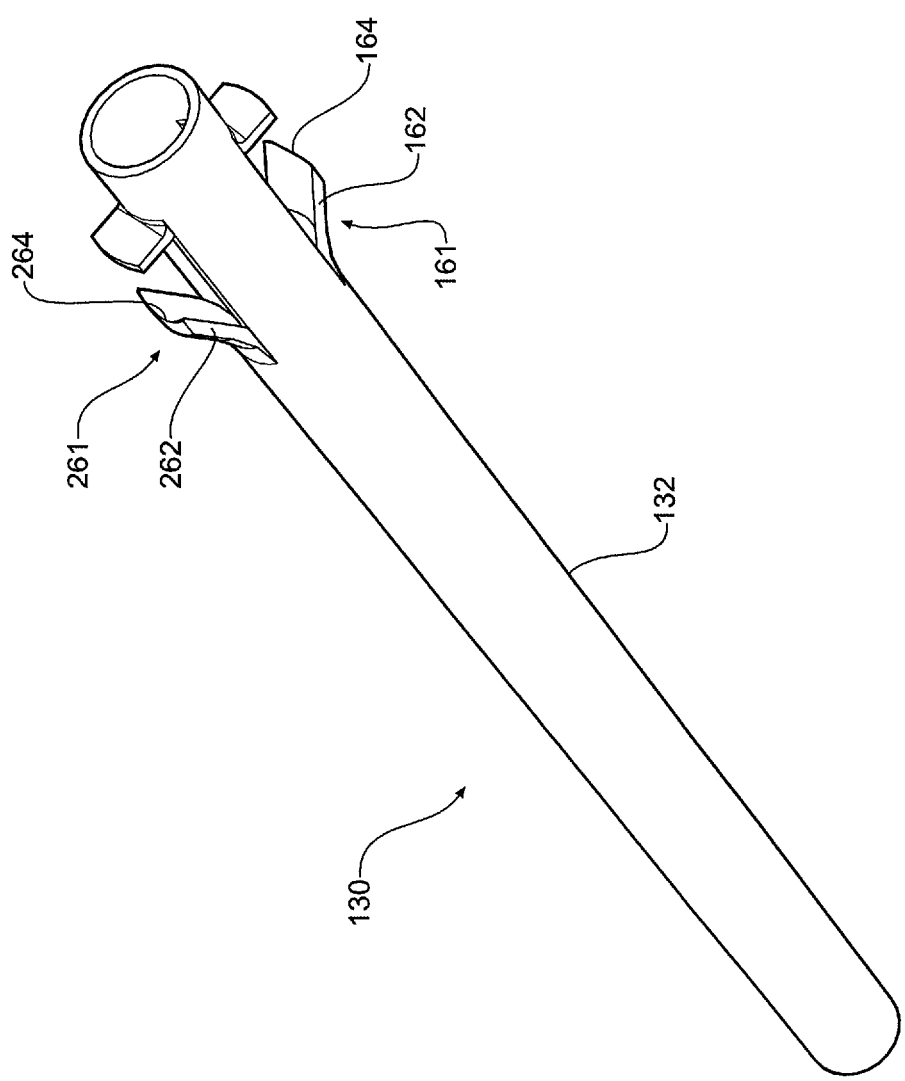

Referring again to FIGS. 1A, 1B, 4 and 5, it can be seen that the tail portion 130 of the capsule assembly 5 includes a tail lock 160. The tail lock is arranged to prevent the lead-in surface 111 of the capsule plug 110 re-entering the capsule tube 52. The tail lock 160 comprises at least one barb 162. In the embodiment of the invention shown in FIGS. 4 and 5, the tail lock 160 comprises a pair of opposed barbs 162 that extend proximally from the tail tube 132, as is most clearly shown in the isometric views of FIGS. 8A and 8B. Each of the aforementioned barbs 162 terminates with a barb abutment surface 164, as is shown in FIG. 8B. The abutment surfaces 164 are resiliently movable from a relaxed position to a deflected position. The relaxed position is shown in FIGS. 8A and 8B. The deflected position enables the abutment surfaces 164 to pass through the wall aperture 54, as is shown in FIG. 1B. FIG. 1B shows the capsule assembly with the capsule tube 52 and capsule wall 53 in their second positions where the abutment surfaces 164 are prevented from re-entering the wall aperture 54 by the abutment of the abutment surfaces 164 against the end wall 53.

Referring again to FIGS. 8A and 8B, it can be seen that the tail portion 130 comprises a tail tube 132 defining a tail lumen 135. The tail tube 132 has a pair of opposed resiliently flexible tabs 161, 261, each tab forming a barb 162, 262.

Figure 4:
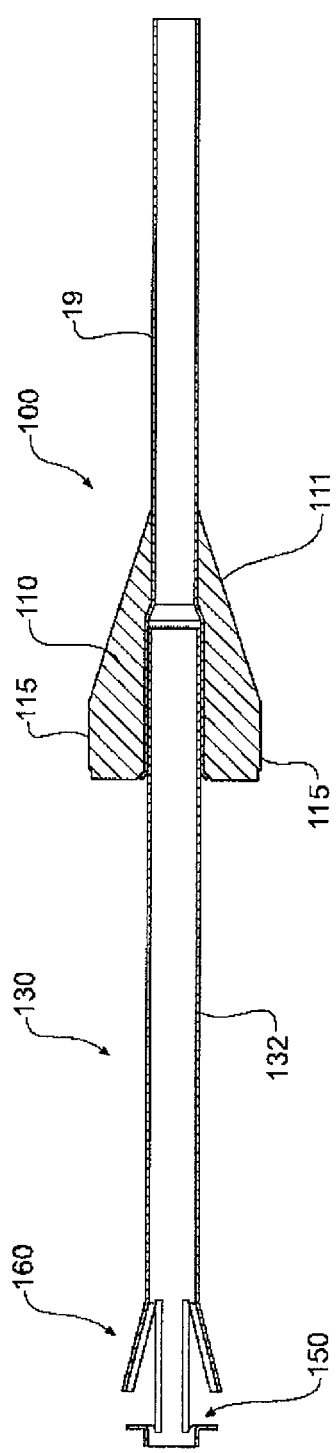
FIG. 4 is a cross-sectional view of a capsule retriever component of the capsule assembly of FIGS. 1A and 1B.

Still referring to FIGS. 8A and 8B, it can be seen that the tail tube 132 also comprises a pair of opposed flanges 152, 252, each flange 152, 252 forming the end stop feature receiver 150 shown in FIG. 4. With the embodiment shown in FIGS. 8A and 8B, the barbs 162, 262 and the flanges 152, 252 are a unitary assembly.

The tail tube 132 may be made from any suitable bio compatible material including stainless steel, nitinol or plastic, for instance.

Turning now to FIG. 3, a system for delivering and deploying an expandable prosthesis in the form of a stent graft 35 is shown. The system includes a sheath 90 having a lumen for receiving a delivery catheter. The system also includes a delivery catheter 10 that includes a longitudinally extending guide wire catheter 11. The delivery catheter 10 is slidably disposed within the lumen of the sheath 90.

The expandable prosthesis in the form of stent graft 35 is disposed on a proximal portion of the delivery catheter 10, as is shown in FIGS. 3 and 10A. A haemostatic device 33 in the form of a Captor™ valve sealingly engaging the delivery catheter 10.

At the proximal most end of the delivery device 1, a nose cone dilator 3 is attached to the guide wire catheter 11 by a guide wire to nose cone attacher 12, as is shown in FIGS. 1A and 1B. the nose cone attacher 12 may be glued to the nose cone dilator 3.

At the proximal portion of the delivery device 1 just distal of the nose cone dilator 3, a capsule assembly 5 is provided, as has been described above.

Referring now to FIGS. 1A, 1B, 3, 4 and 5, it can be seen that there is a plug sleeve 19 joined to the capsule plug portion 110 and mounted coaxially around the guide wire catheter 11. The plug sleeve 19 may be made from a polymer such as polyether ether ether ketone (PEEK) and may be bonded to the capsule plug portion 110 by a suitable adhesive. The guide wire catheter 11 is slidably movable with respect to the capsule plug tail portion 130 and the capsule plug portion 110 from a first position shown in FIG. 1B, in which the distal end 59 of the capsule tube 52 surrounds an opening 57 into the capsule cavity 55 to a second position shown in FIG. 1B, in which the distal end of the capsule tube is adjacent to the lead-in surface of the plug portion 110. In this second position shown in FIG. 1B, the capsule assembly 5 provides a transition from the lead-in surface 111 of the plug portion 110 to the distal end 59 of the capsule tube 52.

Again referring to FIG. 3, it can be seen that from the handle 13 extends a pusher catheter 29 through a sheath manipulator 31 to which is connected the sheath 90. In FIG. 3, the stent graft 35 has been released and all of the trigger wire release devices, which are depicted on the handle in FIG. 2C, have been removed. The guide wire catheter 11 extends from a Luer lock connector 32 at the distal end of the device through the pin vice 15, handle 13 and pusher catheter 29 to nose cone attacher 12 and the nose cone dilator 3 at the proximal end of the delivery device 1.

The nose cone dilator 3 and the capsule tube 52 will generally be fabricated as separate components and then glued together, however they may be fabricated as a unitary component.

The interaction between the abutment surfaces 164, 264 and the capsule end wall 53 provides a compressive resistance. Any relative movement between the capsule tube 52 and the capsule retriever 100, once in the position shown in FIGS. 1B and 10C, will be strongly resisted in compression. This facilitates retraction through a potentially winding and pulsating aorta, past the proximal end 34 of the sheath 90, through the sheath 90 and then through the Captor™ valve 33.

The long tail tube 132 stabilises the entire capsule retriever 100 and further prevents the capsule retriever 100 from dislodging from its retrieval position, as is illustrated in FIG. 1B. It is also effective in ensuring that there remains a smooth transition from the lead-in surface 111 of the capsule plug tip portion 110 to the distal end 59 of the capsule tube 52.

The capsule plug portion 110 may be made from various biocompatible materials including stainless steel. It fits coaxially around the guide wire catheter 11 enabling the guide wire catheter 11 to move longitudinally within the capsule tube 52. The plug sleeve 19 is mounted coaxially around the guide wire catheter 11 and the guide wire catheter 11 can move longitudinally within the plug sleeve 19. At its proximal end, the plug sleeve 19 is joined to the capsule plug portion 110, as is shown in FIGS. 1A and 1B.

Figure 2A:
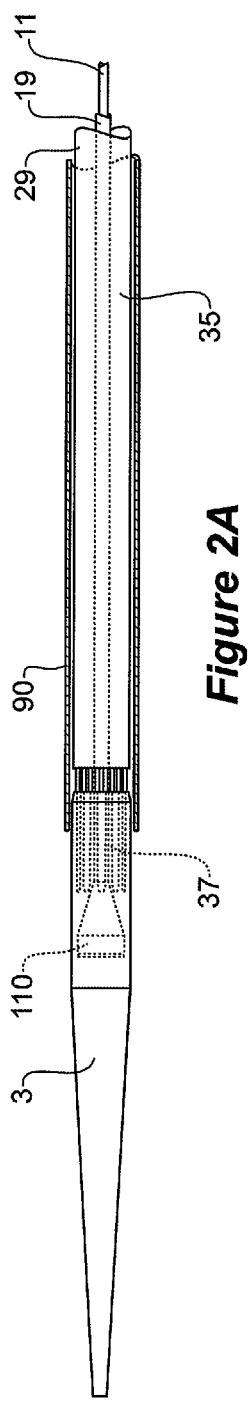
FIGS. 2A and 2B show a proximal end of a delivery device having a capsule assembly, as shown in FIGS. 1A and 1B in the aforementioned first and second positions respectfully.
Figure 2B:
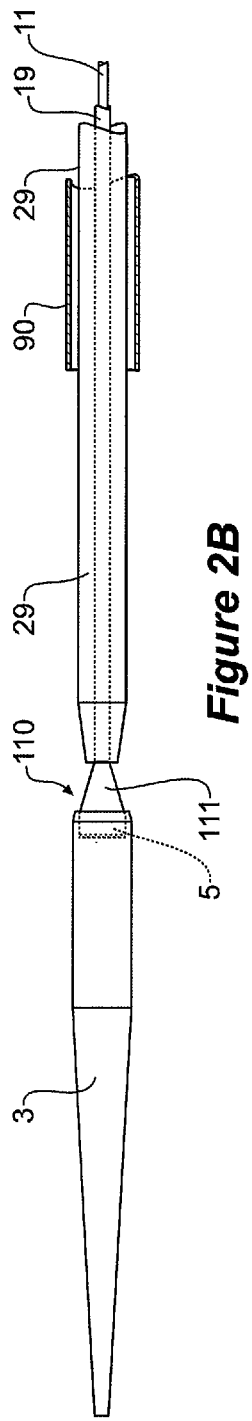
Figure 2C:
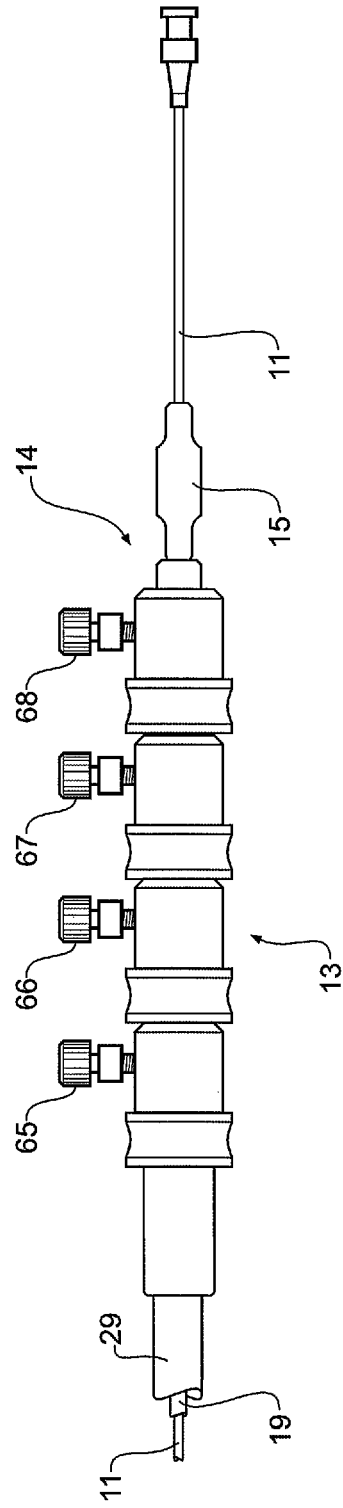
FIG. 2C is a side view of a handle end of the delivery device of FIGS. 2A and 2B.

At its distal end, the plug sleeve 19 terminates at the handle 13 as is diagrammatically illustrated in FIG. 2C.

Figure 9A:
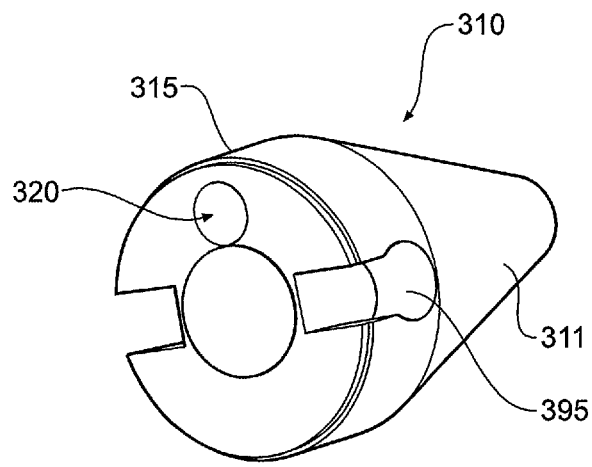
FIG. 9A is an isometric view of an alternative plug portion of the capsule retriever.
Figure 9B:
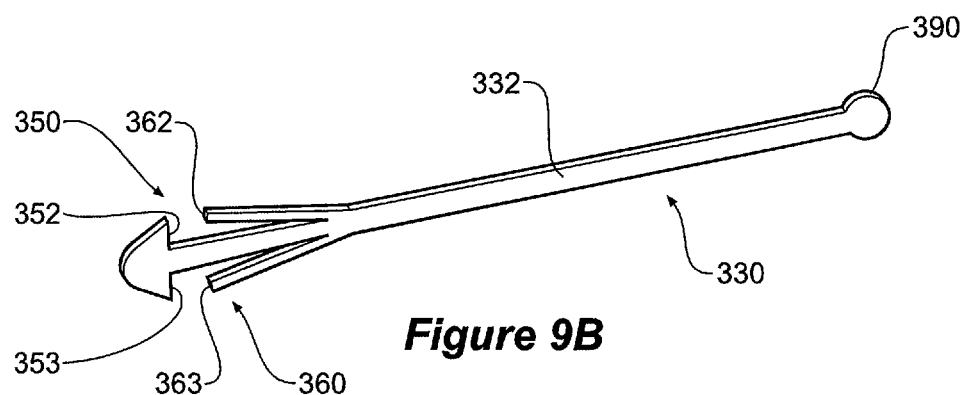
FIG. 9B is an alternative tail portion of the capsule retriever.
Figure 9C:
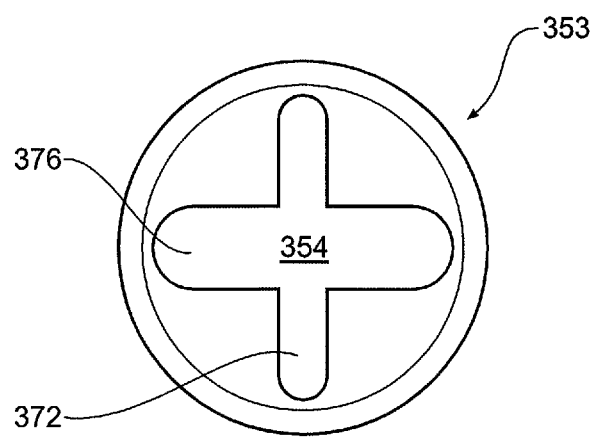
FIG. 9C is an alternative capsule end wall of the capsule retriever.

An alternative capsule retriever having a capsule plug portion 310 is shown in FIGS. 9A, 9B and 9C. With the alternative capsule retriever, a pair of spaced apart parallel tail bars 332 form a capsule plug tail portion 330 that provides a similar function to the tail portion 130 of FIGS. 8A and 8B. The tail heads 390 sit within cavities 395 within the capsule plug portion 310 so as to operably connect the tail bars 332 to the capsule plug portion 310.

A trigger wire lumen 320 is provided in the capsule plug portion 310, as is shown in FIG. 9A.

The alternative capsule plug portion 310 and associated alternative tail portions 332 require an alternative proximal capsule and wall 353, as is shown in FIG. 9C. The alternative proximal capsule end wall 353 includes a tail slot 376 and assembly slot 372. The assembly slot 372 is provided to enable assembly of the various components of the capsule assembly. The tail slot 376 allows limited longitudinal movement of the tail bars 332 but is sized to prevent the end flanges 352 moving through the tail slot 376 in use. Similarly, the tail slot 376 is sized to only allow the barbs 362 to move thought the tail slot in one direction.

In order to better understand how the capsule assembly 5 can be used, the interface between a stent graft 35 and the introducer 1 is shown in more detail in FIGS. 10A, 10B and 10C. These figures show in detailed cross-section a portion of a stent graft delivery device 1 according to an embodiment of the present invention. FIG. 10A is similar to that of FIG. 1A but shows additional detail, including the stent graft 35 and its exposed stent 37. In FIG. 10A, the exposed stent 37 is received into the capsule cavity 55 and is prevented from being prematurely removed from the capsule assembly 5 by the use of a trigger wire 39, which passes through the stent graft 35 to the outside of the capsule assembly 5 and then enters the capsule 5 through aperture 41 in the capsule tube 52. The trigger wire 39 then passes through one of the bends 43 of the exposed stent 37 and then through a hole 56 in the plug portion 110 and into the nose cone cavity 4 in the nose cone dilator 3. The hole 56 is shown in FIG. 6.

In FIG. 10B, the trigger wire 39 has been removed and the nose cone dilator 3 and capsule assembly 5 have been advanced proximally by movement of the guide wire catheter 11, as indicated by the arrow 49 on FIG. 10B with respect to the handle 13. The exposed stent 37 is still partly retained in the capsule. The plug portion 110 has, in effect, moved towards the distal end 59 of the capsule tube 52.

In FIG. 10C, the capsule plug portion 110 is shown fully extended from the capsule tube 52 and is locked in place by the tail lock 160 and the end stop 150. The interaction between the tail lock 160, or more specifically, the barb abutment surfaces 164, 264 shown on FIG. 8B and the proximal capsule end wall 53, provide a compressive resistance. Any relative movement between the capsule tube 52 and the capsule plug 110, once in the position shown in FIGS. 1B and 10C, will be strongly resisted in compression.

The operation of the embodiment of the invention illustrated in FIG. 3 will now be described.

The environment in which the capsule assembly 5 is typically used is within the aorta of a patient, proximal to an aortic aneurism. Blood pulses past the delivery device 1 and, hence the capsule assembly 5, as it tracks through what is often a torturous vasculature towards an incision in the femoral artery.

The delivery system 1 is positioned such that the stent graft 35 is aligned in the area of treatment, which places the nose cone dilator 3 and the capsule assembly 5 proximal to the aneurism. At this point, various stent graft deployment steps are taken as is known in the art and it is only when the proximal stent 37 is ready for deployment, that the capsule retriever 100 of the capsule assembly 5 is activated, as will now be described.

The proximal exposed stent 37 is deployed by removing the trigger wire 39 end by pulling the trigger wire 39 out of the trigger wire lumen 120. The pin vice arrangement 15, shown in FIG. 2C, is then released. The guide wire catheter 11 is then pushed at its distal end in a proximal direction. This movement in the direction of arrow 49, as shown in FIG. 10B, slides the capsule tube 52 off the exposed stent 37 and is stopped when the capsule plug tail portion 130 snaps into locking engagement with the proximal capsule end wall 53 into the position shown in FIG. 1B.

The locking mechanism in the form of pin vice 15 (as is shown in FIG. 3) is reactivated to lock the sleeve 19 and the guide wire catheter 11 together and then the nose cone dilator 3 and capsule assembly 5 are retrieved as the distal attachment of the stent graft 35 is removed, docking the capsule plug portion 110 with the proximal end of the pusher catheter 29 (these components are most clearly shown in FIG. 3). This docked position is shown in FIG. 2B.

In some applications the capsule assembly 5 will form part of a more complex introducer than the introducer 1 illustrated in FIG. 3. For instance, an introducer with a two-part handle such as that shown and described in the applicant's earlier patent publication number US2010/0198328 (Hartley et al.), titled Preloaded Stent Graft Delivery Device, can be used for deployment of fenestrated stent grafts that have fenestrations for branch vessels (the contents of this publication is hereby incorporated by reference in its entirety). Such a handle may resemble the handle shown in FIG. 2C with locking screws 65, 66, 67 and 68 provided for release and trigger wires. With such more complex introducers and their stent grafts, it is not until after cannulation of the fenestrations is complete and associated accessories removed that the pusher catheter 29 is retrieved through the sheath 90 leaving the nose cone dilator 3 and capsule assembly 5 in place until the handle pieces come together. Finally, the nose cone dilator 3 and capsule assembly 5 are removed via the sheath 90 by pulling them through the Captor™ valve 33.

It has been found that the capsule assembly 5 offers a number of advantages over earlier capsule assembly arrangements. For instance, the capsule plug portion 110 is more stable and will not readily dislodge even as the delivery device 1 is manipulated through torturous vasculature systems. Embodiments of the invention described above are relatively simple and easy to manufacture with tight tolerance being less important as compared to prior art designs. With the embodiments of the invention described above, it is extremely unlikely, if not impossible, for the plug portion 110 to come all of the way out of the capsule tube 52. Again, this provides advantages over prior art devices. With embodiments of the invention that include the tail lock 160 described above, the capsule assembly 5 does not rely on tension in the (PEEK) plug sleeve 19 to hold the capsule plug portion 110 in its retrieval position, as is shown in FIG. 1B.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A system for delivering and deploying an expandable prosthesis, the system comprising:
    a prosthesis having proximal and distal ends;
    a nose cone dilator having proximal and distal ends; and
    a capsule assembly coupled to the nose cone dilator, the capsule assembly comprising:
        a capsule retriever having a plug portion and a tail portion, the plug portion having a lead-in surface, the tail portion having an elongate body extending proximally from the plug portion to an end stop feature receiver, wherein the tail portion is closer to the proximal end of the nose cone dilator than the plug portion is to the proximal end of the nose cone dilator;
        a capsule tube having an end stop feature at a proximal end thereof and terminating in a distal end; and
        a capsule cavity inside the capsule tube, the proximal end of the prosthesis being receivable in the cavity,
        wherein the capsule tube is slidably movable with respect to the capsule retriever from a first position in which the distal end of the capsule tube surrounds an opening into the capsule cavity to a second position in which the distal end of the capsule tube is adjacent to the lead-in surface of the plug portion and the end stop feature and end stop feature receiver are engaged.

2. The system as claimed in claim 1, wherein the end stop feature comprises a capsule wall, the capsule wall defining a wall aperture.

3. The system as claimed in claim 1, wherein the lead-in surface includes a frusto-conical portion.

4. The system as claimed in claim 1, wherein the plug portion comprises a landing surface proximally adjacent to the lead-in surface, the landing surface slidably engaging the capsule tube.

5. The system as claimed in claim 1, wherein the tail portion comprises a tail lock, the tail lock arranged to prevent the lead-in surface of the capsule plug portion re-entering the capsule tube from the second position.

6. The system as claimed in claim 5, wherein the tail lock comprises a barb, the barb extending proximally from the elongate body and terminating with a barb abutment surface, the barb abutment surface resiliently moveable from a relaxed position to a deflected position, the deflected position enabling the abutment surface to pass through the wall aperture.

7. The system as claimed in claim 6 wherein, when the capsule tube is in the second position, the abutment surface is prevented from re-entering the wall aperture by abutment of the abutment surface against the end wall.

8. The system as claimed in claim 7, wherein the tail portion comprises a tail tube, the tail tube defining a tail lumen.

9. The system as claimed in claim 8, wherein the tail tube comprises a pair of opposed resiliently flexible tabs, each tab forming one of said barbs.

10. The system as claimed in claim 9, wherein the tail tube comprises a pair of opposed flanges, the flanges forming said end stop receiver.

11. The system as claimed in claim 10, wherein the barbs, the flanges, and the tail tube are a unitary assembly.

12. The system as claimed in claim 1, including a guide wire catheter extending distally from the nose cone dilator through the capsule assembly, a sheath and a handle.

13. A system for delivering and deploying an expandable prosthesis, the system comprising:
    a sheath having a lumen;
    a delivery catheter including a longitudinally extending guide wire catheter, the delivery catheter slidably disposed within the lumen of the sheath;
    an expandable prosthesis disposed on a proximal portion of the delivery catheter;
    a haemostatic device sealingly engaging the delivery catheter; and
    a capsule assembly at the proximal portion of the delivery catheter, the capsule assembly comprising:
    a capsule retriever having a plug portion and a tail portion, the plug portion having a lead-in surface, the tail portion having an elongate body extending proximally from the plug portion to an end stop feature receiver;
    a capsule tube having an end stop feature at a proximal end thereof and terminating in a distal end; and
    a capsule cavity inside the capsule tube, a proximal end of the expandable prosthesis being receivable in the cavity,
    wherein the capsule tube is slidably movable with respect to the capsule retriever from an first position in which the distal end of the capsule tube surrounds an opening into the capsule cavity to a second position in which the distal end of the capsule tube is adjacent to the lead-in surface of the plug portion and the end stop feature and end stop feature receiver are engaged.

14. The system as claimed in claim 13 comprising a plug sleeve joined to the capsule plug portion and mounted coaxially around the guide wire catheter, the guide wire catheter slidably movable with respect to the plug sleeve and the capsule plug portion from the first position to the second position.

15. The as claimed in claim 13, wherein the end stop feature comprises a capsule wall, the capsule wall defining a wall aperture.

16. The as claimed in claim 13, wherein the tail portion comprises a tail lock, the tail lock arranged to prevent the lead-in surface of the capsule plug portion re-entering the capsule tube from the second position.

17. The as claimed in claim 16, wherein the tail lock comprises a barb, the barb extending proximally from the elongate body and terminating with a barb abutment surface, the barb abutment surface resiliently moveable from a relaxed position to a deflected position, the deflected position enabling the abutment surface to pass through the wall aperture.

18. The as claimed in claim 17 wherein, when the capsule tube is in the second position, the abutment surface is prevented from re-entering the wall aperture by abutment of the abutment surface against the end wall.

19. The as claimed in claim 18, wherein the tail portion comprises a tail tube, the tail tube defining a tail lumen.

20. The as claimed in claim 19, wherein the tail tube comprises a pair of opposed resiliently flexible tabs, each tab forming one of said barbs.

21. The as claimed in claim 20, wherein the tail tube comprises a pair of opposed flanges, the flanges forming said end stop receiver.

22. A system for delivering and deploying an expandable prosthesis, the system comprising:
   a sheath having a lumen;
   a delivery catheter including a longitudinally extending guide wire catheter, the delivery catheter slidably disposed within the lumen of the sheath;
   an expandable prosthesis disposed on a proximal portion of the delivery catheter;
   a haemostatic device sealingly engaging the delivery catheter; and
   a capsule assembly at the proximal portion of the delivery catheter, the capsule assembly comprising:
   a capsule tube terminating in a distal end;
   a proximal capsule end wall, the end wall defining a wall aperture and an end stop feature;
   a capsule cavity generally bounded by the capsule tube and the proximal capsule end wall, a proximal end of the expandable prosthesis being receivable in the cavity; and
   a capsule retriever having a plug portion and a tail portion, the plug portion having a lead-in surface, the tail portion having an elongate body extending proximally from the plug portion through the wall aperture and having an end stop feature receiver, the end stop feature and end stop feature receiver mutually engagable.

* * * * *